United States Patent [19]

Immel et al.

[11] 4,181,810
[45] Jan. 1, 1980

[54] PROCESS FOR THE PREPARATION OF PROPANE-1,3-DIOLS, DISUBSTITUTED IN THE 2-POSITION

[75] Inventors: Otto Immel, Krefeld; Hans-Helmut Schwarz, Krefeld-Traar; Oskar Weissel, Krefeld, all of Fed. Rep. of Germany

[73] Assignee: Bayer Aktiengesellschaft, Leverkusen, Fed. Rep. of Germany

[21] Appl. No.: 852,117

[22] Filed: Nov. 16, 1977

[30] Foreign Application Priority Data

Nov. 23, 1976 [DE] Fed. Rep. of Germany ....... 2653096

[51] Int. Cl.² ..................... C07C 29/14; C07C 35/02
[52] U.S. Cl. ................................. 568/807; 260/602; 568/814; 568/821; 568/831; 568/838; 568/862
[58] Field of Search ............................ 260/635 A, 602; 568/862, 831, 814, 821, 838, 807

[56] References Cited
U.S. PATENT DOCUMENTS 2,818,443  12/1957  Robeson ............................ 260/602

OTHER PUBLICATIONS

Durr, "Annales de Chimie", 1956, pp. 84–114.

Cason, "Essential Principles of Organic Chemistry", 1956, pp. 162–167.

Primary Examiner—Joseph E. Evans
Attorney, Agent, or Firm—Sprung, Felfe, Horn, Lynch & Kramer

[57] ABSTRACT

A process for the preparation of a propane-1,3-diol, disubstituted in the 2-position, which comprises contacting an ethanal disubstituted in the 2-position, which ethanal has the formula

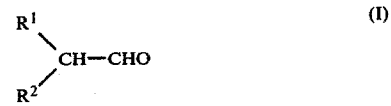
(I)

wherein $R^1$ and $R^2$ are identical or different and denote optionally substituted alkyl, cycloalkyl, aralkyl or aryl radicals or an optionally substituted heterocyclic radical, or together denote an optionally substituted divalent hydrocarbon radical with formaldehyde in the presence of an acid ion exchanger and thereafter contacting the resultant reaction product with hydrogen under hydrogenation conditions.

11 Claims, No Drawings

PROCESS FOR THE PREPARATION OF PROPANE-1,3-DIOLS, DISUBSTITUTED IN THE 2-POSITION

The invention relates to a process for the preparation of propane-1,3-diols, disubstituted in the 2-position, by reacting ethanals, disubstituted in the 2-position, with formaldehyde in the presence of acid ion exchangers and subsequently hydrogenating the reaction product.

It is already known from German Auslegeschrift No. 1,014,098 to prepare 2,2-dimethylpropane-1,3-diol by the alkaline condensation of formaldehyde with isobutyraldehyde, to give formisobutyraldol, and to thereafter reduce the same.

Furthermore, it is known from Annales de Chimie, 13th Series, volume 1 (1956), pages 84 to 114, to carry out the aldol condensation of oenanthaldehyde in the presence of strongly acid ion exchangers, but an aldol condensation between two different aliphatic aldehydes could not be achieved in this manner.

It has now been found that propane-1,3-diols disubstituted in the 2-position are obtained in a simple manner by a process which comprises contacting an ethanal, disubstituted in the 2-position, of the general formula

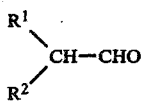

in which $R^1$ and $R^2$ are identical or different and denote an optionally substituted alkyl, cycloalkyl, aralkyl or aryl radical or an optionally substituted heterocyclic radical, or together denote an optionally substituted divalent hydrocarbon radical with formaldehyde in the presence of acid ion exchangers and thereafter hydrogenating the resultant product. This later hydrogenation can be performed in a manner which is in itself known.

Optionally substituted alkyl radicals which may be mentioned are straight-chain and branched alkyl radicals with 1 to 15, preferably 1 to 8 and in particular 1 to 4, carbon atoms, such as methyl, ethyl, propyl, isopropyl, butyl, isobutyl, tert.-butyl, amyl, isoamyl and the further isomeric pentyl radicals and the isomeric hexyl, heptyl and octyl radicals.

Contemplated optionally substituted cycloalkyl radicals are those with 4 to 12, preferably 4 to 8, carbon atoms, in particular cyclopentyl and cyclohexyl.

Contemplated optionally substituted aralkyl radicals are those with 6 or 10 ring carbon atoms and up to 4 carbon atoms in the aliphatic part, preferably benzyl and phenylethyl.

Contemplated optionally substituted aryl radicals are those with 6, 10 and 14 ring carbon atoms, in particular phenyl and naphthyl.

Contemplated optionally substituted heterocyclic radicals are those with 5 to 14 ring members, in particular 5-membered and 6-membered rings, which contain an oxygen atom as the hetero atom.

Contemplated optionally substituted divalent hydrocarbon radicals which can be formed from $R^1$ and $R^2$ together are preferably 4-membered to 12-membered divalent alkyl and alkenyl radicals, in particular the pentamethylene and pent-2-ene-1,5-diyl radical.

In cases where $R^1$ and $R^2$ are substituted alkyl, cycloalkyl, aralkyl or a divalent hydrocarbon forming a ring, substituents such as chloro, bromo or alkoxy groups can be contemplated, preferably methoxy and ethoxy groups.

Examples of compounds of the formula (I) which may be mentioned are: 2-methyl-propanal, 2-methylbutanal, 2-ethylpentanal, 2-ethylhexanal, 2-isopropylbutanal, 2-phenylpropanal, 2-cyclohexylpropanal, 2-phenylbutanal, 2,3-diphenylpropanal, cyclopentylaldehyde, cyclohexylaldehyde and cyclododecylaldehyde.

Preferred starting compounds of the formula I are those in which $R^1$ and $R^2$ are identical or different and represent alkyl radicals with 1 to 12, in particular 1 to 4, carbon atoms or $R^1$ and $R^2$ together form an aliphatic radical with 4 to 7 carbon atoms.

The process according to the invention is carried out in 2 stages.

In the first reaction stage, the compound of the formula (I) is reacted with formaldehyde in the molar ratio 1:5 to 5:1, preferably 1:3 to 3:1, in the presence of an acid ion exchanger; the reaction is illustrated by the equation which follows, using isobutyraldehyde as an example.

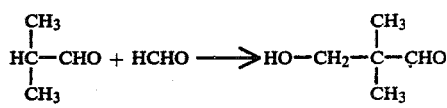

In general, formaldehyde is employed in the form of an aqueous solution, preferably containing from 20 to 40% by weight of formaldehyde, appropriately at the commercially available concentration.

In general, this first stage of the process according to the invention is carried out in the temperature range between normal temperature and the boiling point of the reaction mixture, that is to say between about 20° and 100° C., preferably 40° to 95° C. and in particular from 60° to 90° C.

Acid ion exchangers which can be used are acid synthetic resin ion exchangers, such as are described, for example, in Ullmanns Enzyklopadie der technischen Chemie (Ullmanns Encyclopedia of Industrial Chemistry), 3rd edition, volume 8 (1957), pages 808 to 821 and Houben-Weyl, Methoden der organischen Chemie (Methods of Organic Chemistry), volume I/1 (1958), pages 525 to 529.

Both ion exchangers based on condensates (compare German Patent specification No. 755,119, German Patent specification No. 747,664, German Patent specification No. 734,279 and German Patent specification No. 733,679) and those based on polymers (compare U.S. Pat. Nos. 2,366,007, 3,549,562, Belgian Patent specification No. 590,370, Belgian Patent specification No. 908,247, DT-AS (German Published specification No. 1,113,570 and DT-AS (German Published specification) 1,168,081) can be used.

Those ion exchangers which can be prepared in a known manner by copolymerising styrene and polyvinylbenzene and subsequently sulphonating the copolymer with sulphuric acid or oleum are preferred (compare German Patent specification No. 734,279, German Patent specification No. 747,553, German Patent specification No. 755,119, DT-AS (German Published specification) 1,113,570, U.S. Pat. Nos. 3,549,363 and 3,586,646).

These cation exchangers are employed in the acid form; they are appropriately converted into the acid form by prior treatment with acid in a known manner.

They can be used in any desired form; they are advantageously employed in the form of lumps or as pergranules.

In carrying out the first stage of the process according to the invention, it can be advantageous to add organic solvents to the mixture of the compound of the formula (I) and the aqueous formaldehyde solution in order to achieve a better solubility of the aldehyde of the formula (I) in the aqueous formaldehyde solution or to achieve a homogeneous solution.

The solvents which are known for this purpose can be used as such organic solvents, preferably lower aliphatic alcohols, such as methanol, ethanol, propanol and isopropanol or alicyclic ethers, such as tetrahydrofurane and dioxane.

The appropriate amount of solvent used depends on the nature of the aldehyde of the formula (I) and can easily be appropriately determined by some preliminary experiments.

The first stage of the process according to the invention can be carried out both discontinuously and continuously.

In the discontinuous procedure, for example, the aldehyde of the formula (I) and formaldehyde solution, in the chosen ratio, and if appropriate the organic solvent, are stirred in a stirred vessel, together with the chosen amount of ion exchanger, at the chosen reaction temperature for a definite time.

In this procedure, the necessary reaction time can be between 10 minutes and 6 hours; it depends both on the nature of the aldehyde of the formula (I) used and on the ion exchanger chosen.

In this procedure, it can be advantageous to carry out the reaction only up to a certain conversion, since the rate of reaction in general becomes lower with progressive conversion.

In general, the rate of reaction increases with the amount of exchanger in the reaction mixture. The reaction can still be carried out economically with a relatively large amount of ion exchanger since the exchanger can be easily recovered by simple filtration or centrifugation.

In general, 1 to 60% by weight, preferably 10 to 40% by weight and in particular 10 to 20% by weight, of cation exchanger in the total amount of the reaction mixture are used.

In the continuous procedure, the reaction mixture is passed over the exchanger in a manner which is in itself known. Here it can also be advantageous to allow the mixture to circulate over the ion exchanger and to interrupt the circulation after a number of passes when a certain content of the reaction product in the reaction mixture has been achieved.

In the continuous procedure, of course, the ratio of cation exchanger to starting compounds and solvent, will be different from that described above and depends, in the customary manner, on the way the continuous process is carried out.

The reaction mixture is worked up in the customary manner.

After the ion exchanger has been separated off, it is possible, on the one hand, to feed the reaction mixture without further separation to the subsequent hydrogenation. However, it is advantageous, in particular when the reaction is prematurely interrupted, to separate off unreacted aldehyde, for example by distillation or extraction, and to use it again.

The hydrogenation of the resulting reaction product in the second stage of the process according to the invention is carried out in a manner which is in itself known. It can be carried out both with catalytically activated hydrogen and with nascent hydrogen. Furthermore, the reaction product can also be reduced with alkylamino-boranes and borohydrides of the alkali metals and of the alkaline earth metals.

The hydrogenation is illustrated, by way of example, by the equation which follows, using formisobutyraldol as an example

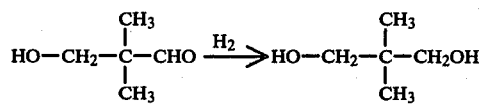

The propane-1,3-diols, disubstituted in the 2-position, obtained by hydrogenation, correspond to the general formula

in which
R$^1$ and R$^2$ have the meaning indicated above.

The reaction product obtained in the first stage of the process according to the invention is preferably hydrogenated in the presence of a hydrogenation catalyst under an increased hydrogen pressure.

In general, the hydrogenation is carried out in the temperature range between room temperature (about 20° C.) and 200° C., preferably from about 50° to 170° C. and in particular between 80° to 130° C. The hydrogen pressure here can be 1 to 500 bars, preferably 50 to 400 bars and in particular 100 to 300 bars.

Hydrogenation catalysts which can be used are those which contain an element of group 8 and/or of subgroup 1 of the periodic system as the catalytically active constituent, that is to say one of the elements iron, cobalt, nickel, ruthenium, rhodium, palladium, osmium, iridium, platinum and/or copper, silver or gold.

Platinum, ruthenium, cobalt, nickel and copper may be preferably mentioned.

These catalysts can be used in the form of skeleton catalysts, supported catalysts or mixed catalysts.

Mixed catalysts based on nickel and cobalt are preferably used, in particular those which contain chromium, aluminium, magnesium, barium, zinc, manganese, thorium and/or copper as further constituents, for example nickel chromite catalysts having the composition Ni-Cr-Al-Cu, Ni-Cr-Zn-Ba and Ni-Cr-Mg-Th-Ba-Cu, or cobalt catalysts having the composition Co-Mg-Cu and Co-Mn-Cu.

The hydrogenation can be carried out in the customary manner both discontinuously and continuously, for example in a stirred autoclave or in a reaction tube. The customary arrangements of apparatuses of the most diverse nature are suitable for carrying out the hydrogenation. It is possible to carry out the hydrogenation as a sump phase process or as a trickle phase process.

In the discontinuous procedure, the hydrogenation is preferably carried out in the customary manner as a sump phase process in an autoclave in the presence of pulverulent catalysts.

The hydrogenation can be particularly advantageously carried out continuously. In this procedure, it is possible, on the one hand, to carry out the reaction in the customary manner using a pulverulent catalyst, for example according to the bubble column principle, in a manner such that the liquid starting material in which the catalyst is suspended is passed through a reactor cascade, together with hydrogen in co-current, or using a catalyst in the form of lumps, for example according to the trickle phase principle, in a manner such that the starting material trickles, in the liquid form, over the stationary catalyst, which is in the reaction tube, whilst the hydrogen is passed through the reaction tube in co-current or counter-current. In this procedure, excess hydrogen can advantageously be recycled.

After the hydrogenation has ended, working up is carried out in the customary manner. The hydrogenation catalyst is appropriately first separated off, for example by filtration. The separation of the propanediol obtained as the reaction product can also be carried out in the customary manner, for example by distillation under reduced pressure.

It can be appropriate here to carry out the distillation in two stages, low-boiling compounds, for example methanol, which has also appropriately formed from excess formaldehyde which has not been removed, and solvents, which have optionally been added in the first reaction stage, being distilled off under normal pressure in the first stage whilst the distillation residue, which contains the propanediol, is subsequently distilled under reduced pressure and the propanediol is isolated. This separation and purification of the propanediol is advantageously carried out under reduced pressure. In this procedure, the pressure and thus the boiling point can advantageously be chosen so that, according to the structure of the propanediol, losses which reduce the yield are avoided under the distillation conditions; the distillation is preferably carried out in the range between 0.1 and 100 mm Hg.

The propane-1,3-diols, disubstituted in the 2-position, of the formula (II), which can be prepared by the process according to the invention, are important industrially as intermediate products for the preparation of plasticisers, lacquer raw materials, polyesters and polyurethanes (compare DT-AS (German Published Specification No.) 1,014,089 and DT-AS (German Published specification No.) 1,800,506).

The cation exchanger, used in Examples 1 to 4 which follow, was a commercially available ion exchanger, present in the form of pergranules and containing sulphonic groups, based on a polystyrene crosslinked with 18% by weight of divinylbenzene (see Belgian Patent specification No. 894,391, Example 3).

EXAMPLE 1

3.615 g (0.032 mol) of cyclohexylaldehyde, 10 g of aqueous formaldehyde solution (about 30% by weight of formaldehyde, 0.1 mol) and 20 g (0.28 mol) of 1,4-dioxane, together with 10 g of the ion exchanger described above, were kept at the boiling point for one hour, whilst stirring and under reflux.

After the reaction, the ion exchanger was filtered off from the reaction liquid and washed with 100 ml of methanol.

The filtrate and wash liquid were brought together, 3.8 g (0.0645 mol) of dimethylamino-borane dissolved in 50 ml of methanol were added and the mixture was boiled under reflux for one hour. Thereafter, the product was evaporated in a rotary evaporator at 50° C. and under a water pump vacuum. A further 20 ml of $CH_3OH$ were then added and the mixture was concentrated again. The residue was analysed. It contained 4.527 g (97.4% of theory) of 1,1-dimethylolcyclohexane.

EXAMPLE 2

220 g (2 mols) of 1,2,5,6-tetrahydrobenzaldehyde, 400 g of a 30% strength by weight aqueous formaldehyde solution (4 mols) and 700 g of dioxane, together with 200 g of the cation exchanger described above, were kept at the boiling point for 6 hours, whilst stirring and under reflux.

119 g of the reaction liquid, filtered from the ion exchanger, were then hydrogenated in an autoclave in the presence of 10 g of a Ni-Cr-Al hydrogenation catalyst at about 110° C., the hydrogen pressure having been kept between 216 and 280 bars.

After the hydrogenation had ended, the reaction solution was analysed by gas chromatography and the analysis was converted for the total mixture.

According to this analysis, the hydrogenated reaction mixture contained 77 mol % of 1,1-dimethylolcyclohexane and 5.1 mol % of hexahydrobenzyl alcohol, corresponding to a yield of 81% of theory of 1,1-dimethylolcyclohexane, relative to the 1,2,5,6-tetrahydrobenzaldehyde reacted.

EXAMPLE 3

144 g (2 mols) of isobutyraldehyde, 500 g of a 30% strength by weight aqueous formaldehyde solution (5 mols), 250 g of 1,4-dioxane and 1 g of hydroquinone, together with 100 g of the cation exchanger described above, were kept at the boiling point for 2 hours, whilst stirring and under reflux.

107 g of the reaction liquid were then separated off and hydrogenated in an autoclave at about 110° C. in the presence of 10 g of a Ni-Cr-Al hydrogenation catalyst, the hydrogen pressure having been kept between 180 and 280 bars.

The hydrogenated reaction mixture was then analysed by gas chromatography and the result was converted for the total mixture. The yield was 87% of theory of 2,2-dimethylpropane-1,3-diol, relative to isobutyraldehyde reacted.

EXAMPLE 4

3 g of the ion exchanger described above were added to 3.01 g (0.042 mol) of isobutyraldehyde, 10 g of a 30% strength by weight aqueous formaldehyde solution (0.1 mol) and 5 g of 1,4-dioxane and the mixture was kept at the boiling point for 3 hours, whilst stirring and under reflux. The reaction mixture was cooled to room temperature, 3.8 g (0.064 mol) of dimethylamino-borane dissolved in 50 ml of methanol were added and the mixture was again kept at the boiling point for one hour. The reaction mixture was then cooled to room temperature and the ion exchanger was filtered off and washed carefully with 24 ml of methanol. The wash liquid and filtrate were combined and the mixture was evaporated in a rotary evaporator at 50° C. and under a water pump vacuum. A further 20 ml of methanol were then added and the mixture was concentrated again. The residue was analysed; it contained 4.261 g (98% of theory) of 2,2-dimethylpropane-1,3-diol.

EXAMPLE 5

220 g (2 mols) of 1,2,5,6-tetrahydrobenzaldehyde, 400 g of a 30% strength by weight aqueous formaldehyde solution (4 mols) and 800 g of 1,4-dioxane, together with 200 g of a commercially available strongly acid ion exchanger (a sulphonated resin based on a bead polymer of styrene containing 2% of divinylbenzene, granule size 0.3–1.2 mm), were kept at the boiling point for 6 hours, whilst stirring.

129 g of the reaction liquid separated off from the ion exchanger were then hydrogenated in an autoclave in the presence of 10 g of an Ni-Cr-Al hydrogenation catalyst, the hydrogen pressure having been kept between 230 and 280 bars.

After the hydrogenation had ended, the reaction solution was analysed by gas chromatography and the analysis was converted for the total mixture. The yield was 72.9% of theory of 1,1-dimethylolcyclohexane, relative to the 1,2,5,6-tetrahydrobenzaldehyde employed.

What is claimed is:

1. A process for the preparation of a propane-1,3-diol, disubstituted in the 2-position, which comprises contacting an ethanal disubstituted in the 2-position, which ethanal has the formula

 (I)

wherein $R^1$ and $R^2$ are identical or different and denote optionally substituted alkyl, cycloalkyl, aralkyl or aryl radicals or an optionally substituted heterocyclic radical, or together denote an optionally substituted divalent hydrocarbon radical at 20° to 100° C. for ten minutes to six hours with formaldehyde in the presence of an acid ion exchanger and thereafter contacting the resultant reaction product with hydrogen under hydrogenation conditions.

2. A process according to claim 1 wherein $R^1$ and $R^2$ are identical or different and represent alkyl radicals with 1 to 12 carbon atoms or together represent a divalent aliphatic radical having 4 to 11 carbon atoms.

3. A process according to claim 1 wherein $R^1$ and $R^2$ are identical or different and represent optionally substituted alkyl radicals of 1 to 15 carbon atoms, optionally substituted cycloalkyl radicals of 4 to 12 carbon atoms, optionally substituted aralkyl radicals where the aryl group contains 6 or 10 carbocyclic carbon atoms and the alkyl group contains up to 4 carbon atoms, optionally substituted aryl radicals where the aryl radical contains 6, 10 or 14 carbocyclic carbon atoms, optionally substituted heterocyclic radicals of 5 to 15 ring members or $R^1$ and $R^2$ taken together form an optionally substituted divalent hydrocarbon radical having 4 to 12 members where the members represent divalent alkylene or alkenylene radicals.

4. A process according to claim 1 wherein said ethanal is selected from the group consisting of 2-methylpropanal, 2-methylbutanal, 2-ethylpentanal, 2-ethylhexanal, 2-isopropylbutanal, 2-phenylpropanal, 2-cyclohexylpropanal, 2-phenylbutanal, 2,3-diphenylpropanal, cyclopentylaldehyde, cyclohexylaldehyde and cyclododecylaldehyde.

5. A process according to claim 1 wherein the process is carried out in two stages, in the first stage the ethanal is reacted with formaldehyde in a molar ratio of 1:5 to 5:1 at a temperature between 20° and 100° C. and thereafter in a second stage the reaction product is hydrogenated.

6. A process according to claim 5 wherein the first stage is carried out at a temperature between 40° and 95° C.

7. A process according to claim 5 wherein the first stage is carried out at a temperature between 60° and 90° C.

8. A process according to claim 1 wherein the hydrogenation is effected upon the reaction product without isolation of any intermediate.

9. A process according to claim 1 wherein the ion exchanger is employed in an amount between 1 and 60 weight percent based upon the weight of the reaction mixture.

10. A process according to claim 9 wherein the acid ion exchanger is present in an amount between 10 and 20 weight percent.

11. A process according to claim 1 wherein hydrogenation is carried out at a temperature between room temperature and 200° C. employing hydrogen at a hydrogen pressure between 1 and 500 bars, employing a hydrogenation catalyst comprising an element of Group VIII and/or of sub-Group I of the Periodic Table.

* * * * *